United States Patent
Chen et al.

(12) 
(10) Patent No.: US 6,274,145 B1
(45) Date of Patent: Aug. 14, 2001

(54) ISOLATED NUCLEIC ACID MOLECULE ENCODING CANCER ASSOCIATED ANTIGEN, THE ANTIGEN ITSELF, AND USES THEREOF

(75) Inventors: Yao-tseng Chen; Matthew Scanlan; Ali Guré; Lloyd J. Old, all of New York, NY (US); Elke Jäger; Knuth Alexander, both of Frankfurt am Main (DE); Jan W. Drijfhout, Leiden (NL); Ozlem Tureci, Homburg/Saar (DE); Ugur Sahin, Homburg/Saar (DE); Michael Pfreundschuh, Homburg/Saar (DE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 08/937,263

(22) Filed: Sep. 15, 1997

Related U.S. Application Data

(63) Continuation-in-part of application No. 08/725,182, filed on Oct. 3, 1996, now Pat. No. 5,804,341.

(51) Int. Cl.[7] .......................... A61K 39/00; A61K 38/04; A61K 45/00; A61K 47/00
(52) U.S. Cl. ................... 424/185.1; 530/328; 424/278.1
(58) Field of Search ............................. 424/185.1, 198.1; 530/328, 327

(56) References Cited

U.S. PATENT DOCUMENTS 4,772,547 * 9/1988 Heimer et al. .
5,057,540 * 10/1991 Kensil et al. .
5,212,085    5/1993 Wands et al. .
5,811,519    9/1998 Lethe et al. .

FOREIGN PATENT DOCUMENTS

WO 95/25122 * 9/1995 (WO) .
WO9918206    4/1999 (WO) .

OTHER PUBLICATIONS

Chen et al., "A testicular antigen aberrantly expressed in human cancers detected by autologous antibody screening", Proc. Natl. Acad. Sci. USA 94: 1914–1918 (3/97).

Kiyokawa et al., "Overexpression of ERK, an EPH Family Receptor Protein Tyrosine Kinase, in Varous Human Tumors[1]", Canc. Res. 54: 3645–3650 (Jul. 15, 1994).

Fazioli et al., "The ezrin–like family of tyrosine kinase substrates: receptor specific pattern of tyrosine phosphorylation and relationship to malignant transformation", Oncogene 8 (5): 1335–1345 (5/93).

Cruse et a. Illustrated Dictionary of Immunology. CRC Press New York, 1995 p. 83.*

Rammensee et al. Immunogenetics 41: 278, 1992.*

* cited by examiner

Primary Examiner—Christina Y. Chan
Assistant Examiner—Marianne DiBrino
(74) Attorney, Agent, or Firm—Fulbright & Jaworski, LLP

(57) ABSTRACT

The invention relates to the isolation of a nucleic acid molecule which encodes a cancer associated antigen. Also a part of the invention is the antigen itself, and the uses of the nucleic acid molecule and the antigen, and peptides derived from it.

8 Claims, 3 Drawing Sheets

FIG. 3

```
            ATCCTCGTGGGCCCTGACCTTCTCTCTGAGAGCCGGGCAGAGGCTCCGGAGC
            Myr      Myr       (P)
             |        |         |
      M  Q  A  E  G  R  G  T  G  G  S  T  G  D  A  D  G  P  G  G
   CATGCAGGCCGAAGGCCGGGGCACAGGGGGTTCGACGGGCGATGCTGATGGCCCAGGAGG

P  G  I  P  D  G  P  G  G  N  A  G  G  P  G  E  A  G  A  T
   CCCTGGCATTCCTGATGGCCCAGGGGGCAATGCTGGCGGCCCAGGAGAGGCGGGTGCCAC

G  G  R  G  P  R  G  A  G  A  A  R  A  S  G  P  G  G  G  A
   GGGCGGCAGAGGTCCCCGGGGCGCAGGGGCAGCAAGGGCCTCGGGGCCGGGAGGAGGCGC

P  R  G  P  H  G  G  A  A  S  G  L  N  G  C  R  C  G  A
   CCCGCGGGGTCCGCATGGCGGCGCGGCTTCAGGGCTGAATGGATGCTGCAGATGCGGGGC
                                                             (P)
                                                              |
      R  G  P  E  S  R  L  L  E  F  Y  L  A  M  P  F  A  T  P  M
   CAGGGGGCCGGAGAGCCGCCTGCTTGAGTTCTACCTCGCCATGCCTTTCGCGACACCCAT

E  A  E  L  A  R  R  S  L  A  Q  D  A  P  P  L  P  V  P  G
   GGAAGCAGAGCTGGCCCGCAGGAGCCTGGCCCAGGATGCCCCACCGCTTCCCGTGCCAGG (P)             (P)
                                     |               |
      V  L  L  K  E  F  T  V  S  G  N  I  L  T  I  R  L  T  A  A
   GGTGCTTCTGAAGGAGTTCACTGTGTCCGGCAACATACTGACTATCCGACTGACTGCTGC

D  H  R  Q  L  Q  L  S  I  S  S  C  L  Q  Q  L  S  L  L  M
   AGACCACCGCCAACTGCAGCTCTCCATCAGCTCCTGTCTCCAGCAGCTTTCCCTGTTGAT

W  I  T  Q  C  F  L  P  V  F  L  A  Q  P  P  S  G  Q  R  R
   GTGGATCACGCAGTGCTTTCTGCCCGTGTTTTTGGCTCAGCCTCCCTCAGGGCAGAGGCG
     *
   CTAAGCCCAGCCTGGCGCCCCTTCCTAGGTCATGCCTCCTCCCCTAGGGAATGGTCCCAG
   CACGAGTGGCCAGTTCATTGTGGGGCCTGATTGTTTGTCGCTGGAGGAGGACGGCTTAC
   ATGTTTGTTTCTGTAGAAAATAAAACTGAGCTACGAAAAA
```

ISOLATED NUCLEIC ACID MOLECULE ENCODING CANCER ASSOCIATED ANTIGEN, THE ANTIGEN ITSELF, AND USES THEREOF

RELATED APPLICATION

This is a continuation-in-part of Ser. No. 08/725,182, filed Oct. 3, 1996 now U.S. Pat. No. 5,804,341, and incorporated by reference.

FIELD OF THE INVENTION

This invention relates to an antigen associated with cancer, and the nucleic acid molecule encoding it, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Acad. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., Kawakami, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. patent applications Ser. No. 08/580,980 now U.S. Pat. No. 5,698,396, and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immnoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has been applied to esophageal cancer samples, and an antigen has now been identified, and its encoding nucleic acid molecule isolated and cloned. The antigen has been found to have more widespread distribution cancer, but had not been found in non-cancerous cells. This, inter alia, is the subject of the invention, which is described in more detail in the disclosure which follows.

BRIEF DESCRIPTION OF THE FIGURES

FIG. 3 shows potential sites for modification of the deduced amino acid sequence SEQ ID NO: 8 of NY-ESO-1.

DETAILED DESCRIPTION OF PREFERRED EMBODIMENTS

EXAMPLE 1

Figures 1A, 1B:
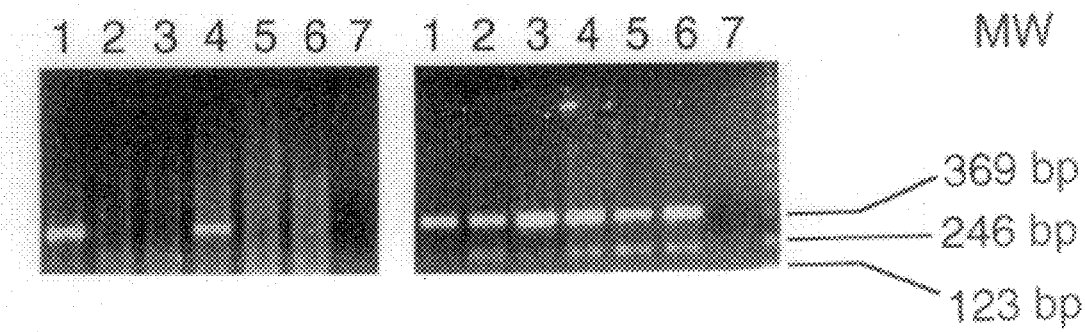
FIG. 1 shows the expression pattern of RNA for the NY-ESO-1 antigen, in various tissue types.
Figure 2:
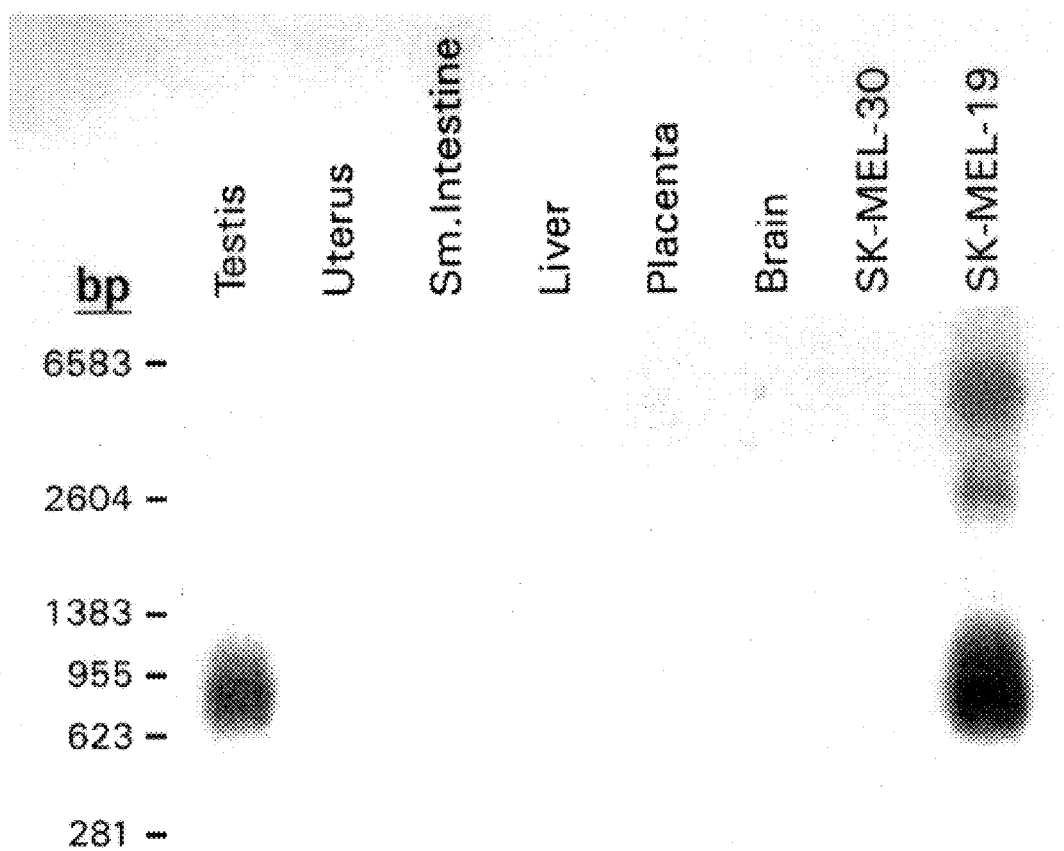
FIG. 2 shows Northern Blot analysis of NY-ESO-1 mRNA, which was found in testis and cell line SK-MEL-19, but not in various other cell and tissue samples.
Figure 4:
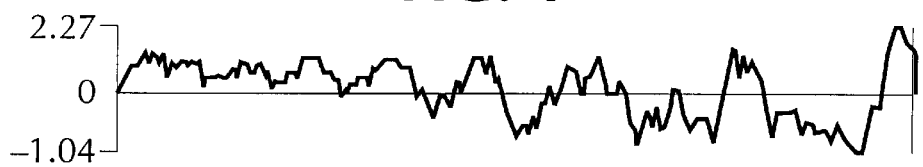
FIG. 4 is a hydrophilicity plot of NY-ESO-1, showing hydrophilic domains in the amino terminus and a long, hydrophobic stretch close to the carboxyl end.

Total RNA was extracted from a snap frozen specimen of well to moderately differentiated squamous cell cancer of the esophagus, using well known methods. See, e.g., Chomzynski, J. Analyt. Biochem. 162: 156–159 (1987), for one such method. This RNA was used to prepare a cDNA library which was then transfected into λZAP phage vectors, in accordance with the manufacturer's instruction. The λZAP library was then transfected into *E. coli*, yielding 1.6×10⁶ primary isolates.

The SEREX methodology of Sahin, et al., Proc. Natl. Acad. Sci. USA 92: 11810–11813 (1995), incorporated by reference, was then used. In brief, autologous serum was stripped of antibodies against molecules which are endogenous to *E. coli* by combining the serum with lysates of *E. coli* transfected with phage λZAP which did not contain the cDNA clones from the esophageal cancer cells.

The depleted serum was then diluted, and mixed with nitrocellulose membranes containing phage plaques. The plaques were incubated overnight, at room temperature. Washing followed, and then the filters were incubated with alkaline phosphatase conjugated goat anti human Feγ secondary antibodies, and reactive phage plaques were visualized by incubating with 5-bromo-4-chloro-indolyl phosphate and nitroblue tetrazolium. A total of 13 positive clones were found.

EXAMPLE 2

Following identification, the reactive clones were subcloned to monoclonality via dilution cloning and testing with human serum. These clones were then purified, excised in vitro, and converted into pBK-CMV plasmid forms, using the manufacturer's instructions. The inserted DNA was then evaluated using EcoRI-XbaI restriction mapping to determine different inserts. Eight different inserts were identified, ranging in size from about 500 to about 1.3 kilobase pairs. The clones were sequenced using an ABI PRISM automated sequencer.

Table 1 summarizes the results. One gene was represented by four overlapping clones, a second by three overlapping clones, and the remaining six by one clone only.

A homology search revealed that the clones referred to as NY-ESO-2, 3, 6, 7 were already known. See Elisei, et al., J. Endocrin. Invest. 16: 533–540 (1993); Spritz, et al., Nucl. Acids Res. 15: 10373–10391 (1987; Rabbits, et al., Nature Genetics 4: 175–180 (1993); Crozat, et al., Nature 363: 640–644 (1993); GenBank H18368 and D25606. Two of the clones (NY-ESO-3 and NY-ESO-6), have previously been shown to be expressed in various normal human tissues. No evidence of lineage restriction has been found. NY-ESO-6 (cDNA), appears to be the 3'-untranslated portion of the FUS/TLS gene. In experiments not reported here, sequencing and Southern Blot analysis of NY-ESO-6 showed no evidence of translocation or point mutations in the cancer. Four of the clones, i.e., NY-ESO-1, 4, 5 and 8 showed no strong homology to sequences in the databases examined, and were thus studied further.

TABLE 1

Genes isolated from esophageal cancer library by immunoscreening with autologous serum

| GENE | CLONE# | size | DNA databank | Comments* |
|---|---|---|---|---|
| NY-ESO-1 | E1-5b | 679 bp | No strong homology | expressed in testis and ovary |
|  | E1-114b | 614 bp |  |  |
|  | E1-153c | 670 bp |  |  |
|  | E1-50 | 679 bp |  |  |
| NY-ESO-2 | E1-71a | 605 bp | U1 small nuclear RNP 1 homolog | cloned by Ab screening (thyroiditis patient) |
|  | E1-140 | 874 bp |  |  |
|  | E1-31 | 750 bp |  |  |
| NY-ESO-3 | E1-141b | 517 bp | Colon 3' direct MboI cDNA; Adult brain cDNA | (dbj D25606, gb H18638) unpublished |
| NY-ESO-4 | E1A-10c | 400 bp | No strong homology | ubiquitous expression in normal tissues |
| NY-ESO-5 | E1A-54 | 670 bp | No strong homology | expressed in normal esophagus |
| NY-ESO-6 | E1B-9b | ~1.2 kb | Human fus mRNA | translocated in liposarcoma t(12;16) |
| NY-ESO-7 | E1B-20f | ~1.0 kb | human U1-70k sn RNP | different from NY-ESO-2 (embl HSU17052, gbM22636) |
| NY-ESO-8 | E1B-20g | ~1.3 kb | No strong homology | ubiquitous expression in normal tissues |

EXAMPLE 3

Studies were carried out to evaluate mRNA expression of the NY-ESO 1, 4, 5 and 8 clones. To do this, specific oligonucleotide primers were designed for each sequence, such that cDNA segments of 300–400 base pairs could be amplified, and so that the primer melting temperature would be in the range of 65–70° C. Reverse Transcription-PCR was then carried out using commercially available materials and standard protocols. A variety of normal and tumor cell types were tested. The clones NY-ESO-4 and NY-ESO-8 were ubiquitous, and were not studied further. NY-ESO-5 showed high level expression in the original tumor, and in normal esophageal tissue, suggesting that it was a differentiation marker.

NY-ESO-1 was found to be expressed in tumor mRNA and in testis, but not normal colon, kidney, liver or brain tissue. This pattern of expression is consistent with other tumor rejection antigen precursors.

EXAMPLE 4

The RT-PCR assay set forth supra was carried out for NY-ESO-1 over a much more complete set of normal and tumor tissues. Tables 2, 3 and 4 show these results. In brief, NY-ESO-1 was found to be highly expressed in normal testis and ovary cells. Small amounts of RT-PCR production were found in normal uterine myometrium, and not endometrium, but the positive showing was not consistent. Squamous epithelium of various cell types, including normal esophagus and skin, were also negative.

When tumors of unrelated cell lineage were tested, 2 of 11 melanomas cell lines showed strong expression, as did 16 of 67 melanoma specimens, 6 of 33 breast cancer specimens and 4 of 4 bladder cancer. There was sporadic expression in other tumor types.

TABLE 2 mRNA distribution of NY-ESO-1 in normal tissues

| Tissue | mRNA | Tissue | mRNA |
|---|---|---|---|
| Esophagus | – | Adrenal | – |
| Brain* | – | Pancreas | – |
| Fetal Brain | – | Seminal Vesicle | – |
| Heart | – | Placenta | – |
| Lung | – | Thymus | – |
| Liver | – | Lymph node | – |
| Spleen | – | Tonsil | – |
| Kidney | – | PBL | – |
| Stomach | – | PBL, activated # | – |
| Small intestine | – | Melanocytes | – |
| Colon | – | Thyroid | – |
| Rectum | – | Uterus | +/–** |
| Breast | – | Testis | + |
| Skin | – | Ovary | + |

*tissues from several parts tested # with IL-2 and PHA
**weakly positive in some specimens, negative by Northern blot

TABLE 3 mRNA distribution of NY-ESO-1 in melanoma and breast cancer cell lines:

| Cell line | NY-ESO-1 mRNA |
|---|---|
| MZ2-MEL3.1 | – |
| MZ2-MEL2.2 | – |
| SK-MEL-13 | – |
| SK-MEL-19 | + |
| SK-MEL-23 | – |
| SK-MEL-29 | – |
| SK-MEL-30 | – |
| SK-MEL-31 | – |
| SK-MEL-33 | – |
| SK-MEL-37 | + |
| SK-MEL-179 | – |
| SK-BR-3 | – |
| SK-BR-5 | – |
| 734B | – |
| MDA-MB-231 | – |

TABLE 4

NY-ESO-1 mRNA expression in various human tumors by RT-PCR

| tumor type | mRNA (positive/total) | tumor type | mRNA (positive/total) |
|---|---|---|---|
| melanoma | 25/77 | ovarian cancer | 2/8 |
| breast cancer | 17/43 | thyroid cancer | 2/5 |
| prostate cancer | 4/16 | bladder cancer | 9/13 |
| colon cancer | 0/16 | Burkitt's lymphoma | 1/2 |
| glioma | 0/15 | basal cell carcinoma | 0/2 |
| gastric cancer | 0/12 | Jejomyosarcoma | 0/2 |
| lung cancer | 5/17 | other sarcomas | 0/2 |
| renal cancer | 0/10 | pancreatic cancer | 0/2 |
| lymphoma* | 0/10 | seminoma | 0/1 |
| hepatoma | 2/7 | spinal cord tumor | 0/1 |

*non-Hodgkin's, non-Burkitt's types.

A further set of experiments were carried out to ascertain if the presence of anti NY-ESO-1 antibody in cancer patient sera could be determined via an ELISA. In brief, recombinant NY-ESO-1 protein, produced via the methods set forth infra, was coated onto solid surfaces, using standard methods. Serum samples were taken from normal patients and patients with various cancers. Anti NY-ESO-1 antibodies should bind thereto. These were then contacted with goat-anti human IgG, labelled with alkaline peroxidase, and then visualized with substrate. The results are presented in the following table:

|  | Eso 1 +/total tested | % |
|---|---|---|
| Cancer patients: |  |  |
| melanoma | 11/127 | 8.7 |
| ovarian cancer | 4/31 | 12.9 |
| lung cancer | 1/24 | 4.0 |
| Blood donors: | 0/70 | 0 |

EXAMPLE 5

Northern blot analysis was then carried out to investigate the size of the NY-ESO-1 transcript, and to confirm tissue expression patterns. The methodology of Ausubel, et al., *Current Protocols In Molecular Biology* (John Wiley & Sons, 1995) was used. To be specific, 20 ug of total RNA per lane were dissolved in a formamide and formaldehyde containing buffer, heated to 65° C., and then separated on a 1.2% agarose gel, with 3% formaldehyde, followed by transfer to nitrocellulose paper. Hybridization was then carried out using a $^{32}$P labelled probe, followed by high stringency washing. The final wash was at 0.1×SSC, 0.1% SDS, 60° C., for 15 minutes.

RNA from testis, and a melanoma cell line (SK-MEL-19) which had been positive for NY-ESO-1 in the prior assays, showed an RNA transcript of about 0.8–0.9 kb. An esophageal carcinoma specimen showed a smear in the 0.4–0.9 kb range, reflecting partial degradation. RNA from additional tissues or cell lines tested showed no transcript.

To get cDNA encoding the full transcript, the esophageal cDNA library was rescreened, using plaque hybridization, and the original cDNA clone as the hybridization probe. When 3×10$^5$ clones were screened, six positives were found. The three longest clones were sequenced. Analysis of open reading frames showed that all three contained the entire coding region, and 5'-untranslated regions of variable size. The longest clone, 755 base pairs in length, (excluding polyA), contains a 543 base pair coding region, together with 53 untranslated bases at the 5' end and 151 untranslated base pairs at the 3'-end. See SEQ ID NO: 1 (also, FIG. 3).

The long ORF indicated that the deduced sequence of NY-ESO-1 protein is 180 amino acids. The single immunopositive clone contained a sequence encoding 173 of these. Deduced molecular mass is 17,995 daltons.

Analysis shows that there is an abundance of glycine residues in the N-terminal portion (30 of the first 80, 4 in the remaining 100). Hydrophilicity analysis indicated that there were hydrophilic antigenic sequences in the N-terminal half of the molecule, with alternating hydrophobic and hydrophilic sequences, ending with a long, C-terminal hydrophobic tail (amino acids 152–172), followed by a short hydrophilic tail. This pattern suggests a transmembrane domain. There are several potential N-myristorylation sites, 3 phosphorylation sites, and no evidence of N-glycosylation sites.

EXAMPLE 6

A melanoma cell line "NW-MEL-38" was established, in 1995, from a patient who suffered from malignant melanoma. Serum samples, peripheral blood lymphocytes, and tumor samples, were taken from the subject and frozen, until the work described herein was carried out. In anticipation of evaluating antitumor T cell response in this patient, the patient was HLA typed as HLA-A1 and HLA-A2.

To determine whether melanoma from this patient expressed NY-ESO-1, total RNA was isolated from both tumor samples and cell line NW-MEL-38, using standard techniques. Then, two micrograms of the total RNA, from each samples were subjected to cDNA synthesis, again using standard techniques.

The cDNA was then used in RT-PCR experiments, using the following primers:
5'-CACACAGGAT CCATGGATGC TGCAGATGCG G'-3' (SEQ ID NO: 2), and
CACACAAAGC TTGGCTTAGC GCCTCTGCCC TG-3' (SEQ ID NO: 3)
These primers should amplify a segment of SEQ ID NO: 1 which spans nucleotides 271 to 599.

Amplification was carried out over 35 cycles, using an annealing temperature of 60° C. The PCR products were visualized via ethidium bromide staining, on a 1.5% agarose gel.

The results indicated that both the tumor and the cell line expressed SEQ ID NO: 1. The cell line and tumor samples were used in subsequent experiments.

EXAMPLE 7

The isolated cDNA molecule, discussed supra, was then used to make recombinant protein. Specifically, the cDNA was PCR amplified, using standard techniques, and was then cloned into a commercially available plasmid vector, i.e., pQE9, which contains His tags. In work not elaborated upon herein, a second vector, pQE9K was also used. This differs from PQE9 in that kanamycin resistance is imparted by pQE9K, rather than ampicillin resistance.

The plasmid vector was transformed into $E. coli$ strain XL1-Blue, and positive transformants were identified via restriction mapping and DNA sequencing. Production of recombinant protein was induced using isopropyl β-D-thiogalactoside, and the protein was purified on an $Ni^{2+}$ ion chromatography column, following well known procedures. The protein, when analyzed via 15% SDS-PAGE and silver staining, was identified as a protein with a molecular weight of about 22 kilodaltons. This is consistent with the anticipated size of the protein from its sequence.

Eukaryotic transfectants were then produced. To do this, the NY-ESO-1 coding sequence was isolated from the pQE9 vector described supra, and then cloned into BamHI-HindIII sites of eukaryotic expression vector pcDNA 3.1. Next, COS-7 cells were transfected with this vector, by contacting cell samples with 150 ng of the plasmid discussed supra, and 150 ng of plasmid pcDNA 1 Amp, which contained either cDNA for HLA-A2.1 or cDNA for HLA-A1, The well known DEAE-dextran chloroquine method was used. The cells were then incubated at 37° C., for 48 hours, after which they were tested in a CTL stimulation assay. Specifically, the assay followed Traversari et al, Immunogenetics 35: 145–148 (1992), incorporated by reference. In brief, 2500 CTLs, (NW38-IVS-1, see example 9, infra), in 100 ul RPMI supplemented with 100% human serum, and 25 U/ml of recombinant IL-2 were added to microwells containing COS-7 transfectants (20,000 cells/well). After 24 hours, 50 ul of supernatant were collected from each well, and TNF-α levels were determined in a standard assay, i.e., one where cytotoxicity against WEHI 164 clone 13 cells were tested, using MTT. Positive cells were used in the Western Blot analysis, described in the example which follows.

The CTLs used were CTL NW38-IVS-1, prepared in accordance with Knuth et al., Proc. Natl. Acad. Sci. USA 81: 3511–3515 (1984), incorporated by reference. Specifically, mixed lymphocyte T cell cultures were set up, by combining $10^5$ autologous NW38 MEL-1 tumor cells, and $10^6$ peripheral blood lymphocytes, taken from the subject. The cytokine IL-2 was added, and the mixed culture was incubated for one week at 37° C. Tumor cells were removed, and a new aliquot of $5 \times 10^4$ tumor cells were added together with IL-2. This process was repeated weekly, until a strong response was seen when tested against $^{51}Cr$ labelled NW-MEL-38 cells. The responder T cells were collected and frozen until used in further experiments.

EXAMPLE 8

Western Blot analysis was then carried out, using the serum samples described supra, as well as cell lysates taken from the cell line NW-MEL-38, described supra, the COS-7 transfectants, described supra, and the purified recombinant protein, also described supra. Serum samples were taken from various points of the patient's therapy. There was no difference in the results.

In these assays, 1 ug of recombinant NY-ESO-1 protein, or 5 ul of cell lysates of either type were diluted in SDS and boiled for five minutes, and then electrophoresed on a 15% SDS gel. After overnight blotting on nitrocellulose (0.45 um), and blocking with 3% BSA, the blots were incubated with serum, diluted at 1:1000, 1:10,000, and 1:100,000, or with a monoclonal antibody against NY-ESO-1, diluted to 1:50, as a positive control. The monoclonal antibody was prepared as follows. BALB/C mice were immunized via five subcutaneous injections of recombinant NY-ESO-1 protein, at 2–3 week intervals. The immunizing formulation included 50 ug of recombinant protein in adjuvant. The first injection used Complete Freund's Adjuvant, and Incomplete Freund's Adjuvant was used thereafter. Spleen cells were taken from the immunized mice, and fused with mouse myeloma cell line SP2/0, to generate hybridomas.

Once hybridomas were generated, they were cloned, and their supernatants were screened against recombinant protein, using a standard solid phase ELISA on microtiter plates. The assay was in accordance with Dippold et al., Proc. Natl. Acad. Sci. USA 77: 6114–6118 (1980), incorporated by reference. A series of negative controls were also run, using recombinant NY-ESO-1. Serum antibodies which bound to recombinant protein, produced by $E. coli$ as described, supra were visualized using goat anti-human IgG, labelled with alkaline phosphatase at 1:10,000 dilution, and were then visualized with NBT-phosphate. Untransfected COS-7 cells were used as a control. Serum from a healthy individual was also used as a control.

Strong reactivity against the recombinant protein was found at serum dilutions down to 1:100,000, and there was also reactivity against lysate of NW-MEL-38. There was no reactivity found against the untransfected COS-7 cells, nor did the serum from a healthy individual show reactivity.

EXAMPLE 9

In the testing of the COS-7 transfectants, supra, and the assays discussed in this example, a cytolytic T cell line "NW38-IVS-1" was used. This "CTL" was generated, via in vitro stimulation of the peripheral blood lymphocytes mentioned supra, using the tumor cell line NW-MEL-38. This was done using standard techniques.

Figure 5:
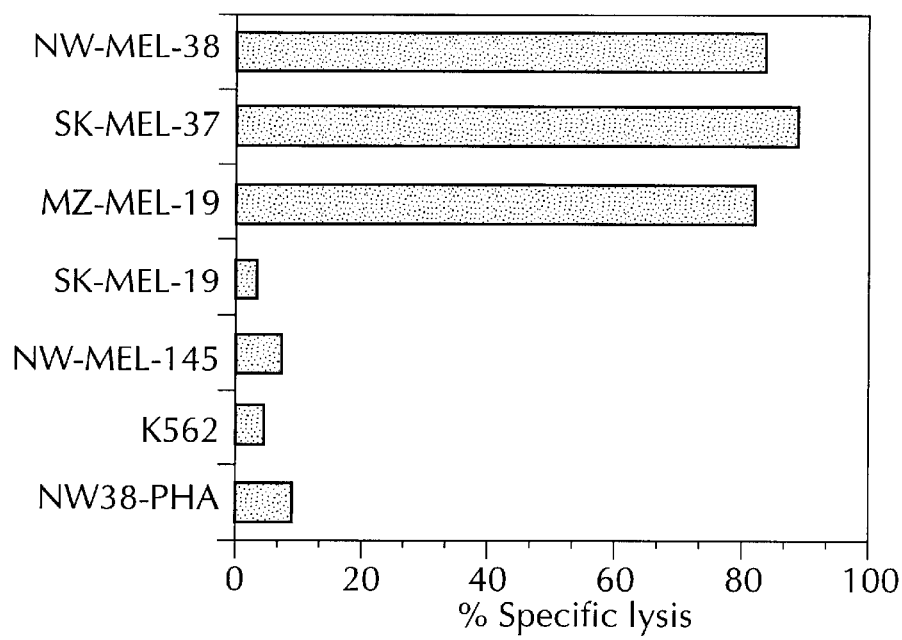
FIG. 5 shows the results of CTL lysis studies using various cells which are HLA-A2 positive, NY-ESO-1 positive, positive for both, or positive for neither.

The CTL was used in a cytotoxicity assay with NW-MEL-38 (which was HLA-A1, A2 positive, and NY-ESO-1 positive), along with two allogeneic cell lines which were NY-ESO-1 and HLA-A2 positive (SK-MEL-37 and MZ-MEL-19), a cell line which is MHC Class I negative (SK-MEL-19), a cell line which is HLA-A2 positive, but NY-ESO-1 negative (NW-MEL-145), along with control cell lines K562 and autologous phytohemagglutinin stimulated blasts. Various effector/target ratios were used, and lysis of $^{51}$Cr labelled target cells was the parameter measured. FIG. 5 shows this.

Figure 6:
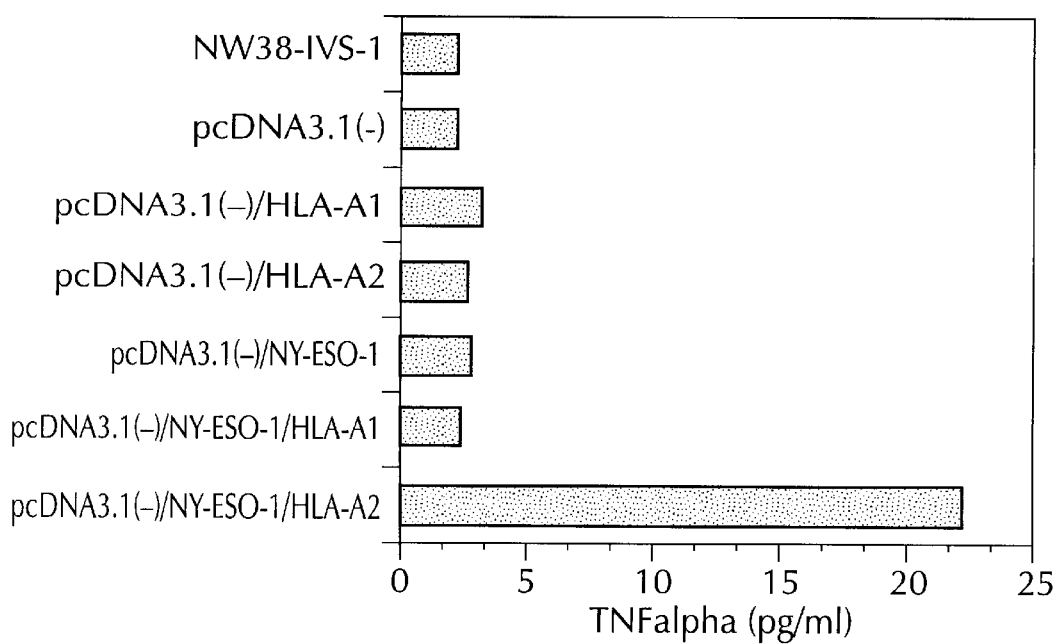
FIG. 6 presents data establishing that HLA-A2 is the presenting molecule for presentation of SEQ ID NO: 1 derived peptides.

The results indicated that the CTL NW38-IVS-1 lysed both the autologous cell line NW MEL-38, and the allogeneic cell lines which were HLA-A2 and ESO-1 positive. Hence, the CTL was reactive with allogeneic materials. See FIG. 6.

EXAMPLE 10

As patient NW38 was HLA-A1 and HLA-A2 positive, experiments were carried out to determine which MHC molecule was the presenting molecule.

The same experiment, described supra, with COS-7 cells was carried out, except that, in these experiments, care was taken to secure separate groups of cotransformants which had been transformed with either HLA-A1 cDNA, or HLA-A2 cDNA, but not both. These results show that the CTL NW38-IVS-1 lysed COS-7 transfectants containing both NY-ESO-1 and HLA-A2 exclusively. See FIG. 6. The work also confirmed the specificity of the CTL, since the NY-ESO-1 negative, HLA-A2 positive cells described in Example 9 were positive for other molecules known to be processed to peptides presented by HLA-A2 molecules.

EXAMPLE 11

Once the presenting MHC molecule was identified as HLA-A2, a screening of the amino acid sequence for NY-ESO-1 was carried out, to identify all peptides which satisfy this motif, using the model set forth by D'Amaro et al., Human Immunol. 43: 13–18 (1995), and Drijfhout, et al., Human Immunol. 43: 1–12 (1995) incorporated by reference.
Peptides corresponding to all of the amino acid sequences deduced thereby were synthesized, using standard techniques, and were then used in cytotoxicity assays, following Knuth et al., Proc. Natl. Acad. Sci. USA 81: 3511–3515 (1984), incorporated by reference. Specifically, cell line CEMX721.174.T2 ("T2" hereafter), was used, because it does not process antigens to MHC complexed peptides, thereby making it ideal for experiments of the type described herein. Samples of T2 cells were labelled with 100 uCi of Na($^{51}$Cr)O$_4$, using standard methods, and were then washed three times, followed by incubation with 10 ug/ml peptide and 2.5 ug/ml of α2-microglobulin. Incubation was for one hour, at room temperature. Then responder cells (100 ul of a suspension of CTL NW38-IVS-1) were added, at an effector/target ratio of 90:1, and incubated for four hours in a water saturated atmosphere, with 5% CO$_2$, at 37° C. Then, plates were centrifuged at 200×g for five minutes, 100 ul of supernatant was removed, and radioactivity was measured. The percentage of $^{51}$Cr release was determined in accordance with known strategies. It was found that the peptides SLLMWITQCFL (SEQ ID NO: 4), SLLMWITQC (SEQ ID NO: 5), and QLSLLMWIT (SEQ ID NO: 6), were the three best stimulators of CTLs. Comparable results were found when NW-MEL-38 and cell lines SK-MEL-37 and MZ-MEL-19 were used as targets, as is shown, supra.

The foregoing examples describe the isolation of a nucleic acid molecule which encodes an esophageal cancer associated antigen. "Associated" is used herein because while it is clear that the relevant molecule was expressed by esophageal cancer, other cancer types, such as melanoma, breast, prostate and lung also express the antigen.

The invention relates to those nucleic acid molecules which encode antigens as described, and which hybridize to reference sequence SEQ ID NO: 1 under stringent conditions. "Stringent conditions" as used herein refers to conditions such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

Also a part of the invention are expression vectors which incorporate the nucleic acid molecules of the invention, in operable linkage (i.e., "operably linked") to a promoter. Construction of such vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used.

Also a part of the invention is the antigen described herein, both in original peptide form and in post translational modified form. The molecule is large enough to be antigenic without any posttranslational modification, and hence it is useful as an immunogen, when combined with an adjuvant (or without it), in both precursor and post-translationally modified forms. The antibodies produced using this antigen, both poly and monoclonal, are also a part of the invention as well as hybridomas which make the monoclonal antibody. It can be used therapeutically as the whole protein, or in portions, as discussed infra. Also a part of the invention are antibodies against this antigen, be these polyclonal, monoclonal, reactive fragments, such as Fab, F(ab)$_2$' and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology so, too, could one assay for the expression of the antigen via any of the standard nucleic acid hybridization assays which are well known to the art, and need not be elaborated upon herein. One could assay for antibodies against the subject molecule, using standard immunoassays as well.

Analysis of SEQ ID NO: 1 will show that there are 5' and 3' non coding regions presented therein. The invention relates to those isolated nucleic acid molecules which contain at least the coding segment, i.e., nucleotides 54–593, and which may contain any or all of nucleotides 1–53 and/or 594–747 of SEQ ID NO: 1.

Further analysis, as discussed supra, reveals that the molecule is processed to peptides which provoke lysis by cytolytic T cells. Example 11 showed how this type of motif analysis can be carried out for HLA-A2 molecules. There has been a great deal of work in motifs for various MHC or HLA molecules, which is applicable here. Hence, a further aspect of the invention is a therapeutic method, wherein one or more peptides which bind to an HLA molecule on the surface of a patient's tumor cells are administered to the patient, in an amount sufficient for the peptides to bind to the MHC/HLA molecules, and provoke lysis by T cells. The exemplification given supra for HLA-A2 molecules is by no means the only type of this administration that can be used. Any combination of peptides may be used. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF and interleukins, and so forth may also be used. Further, these peptides and proteins may be formulated into vaccines with the listed material, as may dendritic cells, or other cells which present relevant MHC/peptide complexes.

Similarly, the invention contemplates therapies wherein the nucleic acid molecule which encodes NY-ESO-1 is incorporated into a vector, such as an adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of NY-ESO-1, simply by monitoring levels of the protein, its expression, and so forth using any or all of the methods set forth supra.

It should be clear that these methodologies may also be used to track the efficacy of a therapeutic regime. Essentially, one can take a baseline value for the NY-ESO-1 protein, using any of the assays discussed supra, administer a given therapeutic agent, and then monitor levels of the protein thereafter, observing changes in ESO-1 levels as indicia of the efficacy of the regime.

As was indicated supra, the invention involves, inter alia, the recognition of an "integrated" immune response to the NY-ESO molecule. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an antibody response. As is indicated, supra, an increase in antibody titer may be taken as an indicia of progress with a vaccine, and vice versa. Hence, a further aspect of the invention is a method for monitoring efficacy of a vaccine, following administration thereof, by determining levels of antibodies in the subject which are specific for the vaccine itself, or a large molecules of which the vaccine is a part.

The identification of NY-ESO-1 proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of NY-ESO-1 proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

Also a part of the inventions are peptides, which can be nonamers, decamers, or undecamers defined as having a core sequence:

LLMWIT (SEQ ID NO: 7)

which have at least one additional residue terminal to the first L residue, preferably serine, and may have as many as three, wherein serine is linked to L to form -SL-, and 0–4 additional amino acids at the C-terminus which, as shown supra, bind to HLA-A2 molecules, thereby provoking a CTL response. These peptides may be used therapeutically, via administration to a patient who is HLA-A2 positive, and expresses NY-ESO-1 in connection with a pathology, as well as diagnostically, i.e., to determine if HLA-A2 positive cells are present, or if relevant CTLs are present, and so forth.

The HLA-A2 molecule is an MHC Class I molecule, and T cells which respond to complexes of peptides and class I molecules are generally $CD8^+$ cells. Another subset of T cells, $CD4^+$ cells, responds to complexes of MHC-Class II molecules and peptides, and MHC-Class II restricted $CD4^+$ T cell responses against recombinant NY-ESO-1, presented by autologous cultured dendritic cells have been detected in melanoma patients. Specifically, in results not described herein, $CD4^+$ cells were separated from other cells from PBLs or serum samples, using well known techniques. Then, they were admixed with dendritic cells which had been pulsed with NY-ESO-1 protein. Proliferation of $CD4^+$ cells was observed, bringing another facet to the integrated immune response discussed herein. Hence, a further aspect of this invention are these $CD4^+$ T cells, peptides which bind to the MHC-Class II molecules, and their use in therapy.

Other features and applications of the invention will be clear to the skilled artisan, and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated peptide which binds to an HLA molecule, wherein the amino acid sequence of said peptide consists of SEQ ID NO. 5 or SEQ ID NO: 6.

2. The isolated peptide of claim 1 wherein said HLA molecule is HLA-A2.

3. An immunogenic composition comprising the isolated peptide of claim 1, and a pharmaceutically acceptable adjuvant.

4. The immunogenic composition of claim 3, wherein said adjuvant is a saponin, an interleukin, or GM-CSF.

5. The immunogenic composition of claim 3, comprising a plurality of peptides which complex with HLA-A2 molecules.

6. An immunogenic composition comprising at least one isolated peptide of claim 1, and a pharmaceutically acceptable adjuvant.

7. The immunogenic composition of claim 6, wherein said adjuvant is a saponin, an interleukin, or GM-CSF.

8. The immunogenic composition of claim 3, comprising both of the peptides defined by SEQ ID NO: 5 and SEQ ID NO: 6.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 752 base pairs
      (B) TYPE: nucleic acid
      (C) STRANDEDNESS: single
      (D) TOPOLOGY: linear (xi) SEQUENCE DESCRIPTION: SEQ ID NO: 1:

```
ATCCTCGTGG GCCCTGACCT TCTCTCTGAG AGCCGGGCAG AGGCTCCGGA GCCATGCAGG      60

CCGAAGGCCG GGGCACAGGG GGTTCGACGG GCGATGCTGA TGGCCCAGGA GGCCCTGGCA     120

TTCCTGATGG CCCAGGGGGC AATGCTGGCG GCCCAGGAGA GGCGGGTGCC ACGGGCGGCA     180

GAGGTCCCCG GGGCGCAGGG GCAGCAAGGG CCTCGGGGCC GGGAGGAGGC GCCCCGCGGG     240

GTCCGCATGG CGGCGCGGCT TCAGGGCTGA ATGGATGCTG CAGATGCGGG GCCAGGGGGC     300

CGGAGAGCCG CCTGCTTGAG TTCTACCTCG CCATGCCTTT CGCGACACCC ATGGAAGCAG     360

AGCTGGCCCG CAGGAGCCTG GCCCAGGATG CCCCACCGCT TCCCGTGCCA GGGGTGCTTC     420

TGAAGGAGTT CACTGTGTCC GGCAACATAC TGACTATCCG ACTGACTGCT GCAGACCACC     480

GCCAACTGCA GCTCTCCATC AGCTCCTGTC TCCAGCAGCT TTCCCTGTTG ATGTGGATCA     540

CGCAGTGCTT TCTGCCCGTG TTTTTGGCTC AGCCTCCCTC AGGGCAGAGG CGCTAAGCCC     600

AGCCTGGCGC CCCTTCCTAG GTCATGCCTC CTCCCCTAGG GAATGGTCCC AGCACGAGTG     660

GCCAGTTCAT TGTGGGGGCC TGATTGTTTG TCGCTGGAGG AGGACGGCTT ACATGTTTGT     720

TTCTGTAGAA AATAAAACTG AGCTACGAAA AA                                   752
```

(2) INFORMATION FOR SEQ ID NO: 2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (xi) SEQUENCE DESCRIPTION: SEQ ID NO: 2:

```
CACACAGGAT CCATGGATGC TGCAGATGCG G                                     31
```

(2) INFORMATION FOR SEQ ID NO: 3:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (xi) SEQUENCE DESCRIPTION: SEQ ID NO: 3:

```
CACACAAAGC TTGGCTTAGC GCCTCTGCCC TG                                    32
```

(2) INFORMATION FOR SEQ ID NO: 4:

(i) SEQUENCE CHARACTERISTICS:
      (A) LENGTH: 11 amino acids
      (B) TYPE: amino acid
      (D) TOPOLOGY: linear (xi) SEQUENCE DESCRIPTION: SEQ ID NO: 4:

Ser Leu Leu Met Trp Ile Thr Gln Cys Phe Leu
                 5                  10

(2) INFORMATION FOR SEQ ID NO: 5:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 5:

Ser Leu Leu Met Trp Ile Thr Gln Cys
                 5

(2) INFORMATION FOR SEQ ID NO: 6:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 6:

Gln Leu Ser Leu Leu Met Trp Ile Thr
                 5

(2) INFORMATION FOR SEQ ID NO: 7:

(i) SEQUENCE CHARACTERISTICS:
        (A) LENGTH: 6amino acids
        (B) TYPE: amino acid
        (D) TOPOLOGY: linear (xi) SEQUENCE DESCRIPTION: SEQ ID NO: 7:

Leu Leu Met Trp Ile Thr
                 5

(2) INFORMATION FOR SEQ ID NO: 8:

(i) SEQUENCE CHARACTERISTICS:
        (A) LENGTH: 180
        (B) TYPE: amino acid
        (D) TOPOLOGY: linear (xi) SEQUENCE DESCRIPTION: SEQ ID NO: 8:

Met Gln Ala Glu Gly Arg Gly Thr Gly Gly Ser Thr Gly Asp Ala Asp
                 5                  10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Ala Pro Arg Gly Ala
                35                  40                  45

Gly Ala Ala Arg Ala Ser Gly Pro Gly Gly Gly Ala Pro Arg Gly Pro
         50                  55                  60

His Gly Gly Ala Ala Ser Gly Leu Asn Gly Cys Cys Arg Cys Gly Ala
 65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

-continued

```
Leu Gln Leu Ser Ile Ser Ser Cys Leu Gln Gln Leu Ser Leu Leu Met
145             150             155             160

Trp Ile Thr Gln Cys Phe Leu Pro Val Phe Leu Ala Gln Pro Pro Ser
            165             170             175

Gly Gln Arg Arg
            180
```